(12) United States Patent
Kosugi et al.

(10) Patent No.: US 10,185,138 B2
(45) Date of Patent: Jan. 22, 2019

(54) IMAGING APPARATUS (71) Applicant: Sony Corporation, Tokyo (JP)

(72) Inventors: Hiroshi Kosugi, Kanagawa (JP); Shuzo Sato, Kanagawa (JP); Eiji Otani, Kanagawa (JP); Mitsuru Sato, Kanagawa (JP)

(73) Assignee: Sony Corporation (JP)

( * ) Notice: Subject to any disclaimer, the term of this patent is extended or adjusted under 35 U.S.C. 154(b) by 191 days.

(21) Appl. No.: 15/231,288

(22) Filed: Aug. 8, 2016

(65) Prior Publication Data
US 2017/0003494 A1   Jan. 5, 2017

Related U.S. Application Data (63) Continuation of application No. 13/670,611, filed on Nov. 7, 2012, now abandoned.

(30) Foreign Application Priority Data

Nov. 14, 2011 (JP) .................. 2011-248694

(51) Int. Cl.
*G02B 23/24* (2006.01)
*H04N 13/207* (2018.01)
*H04N 13/257* (2018.01)
*A61B 1/00* (2006.01)
*A61B 1/04* (2006.01)
(Continued)

(52) U.S. Cl.
CPC ...... *G02B 23/2415* (2013.01); *A61B 1/00193* (2013.01); *A61B 1/04* (2013.01); *G02B 5/201* (2013.01); *G02B 23/2453* (2013.01); *G02B 23/2484* (2013.01); *G02B 27/286* (2013.01); *G06T 3/4015* (2013.01); *H04N 5/2256* (2013.01); *H04N 13/207* (2018.05); *H04N 13/257* (2018.05); *H04N 2005/2255* (2013.01); *H04N 2213/001* (2013.01)

(58) Field of Classification Search
None
See application file for complete search history.

(56) References Cited

U.S. PATENT DOCUMENTS 3,827,793 A   8/1974 Dudley
5,385,138 A   1/1995 Berry
(Continued)

FOREIGN PATENT DOCUMENTS

CN   2470846 Y   1/2002
CN   101995758 A   3/2011
(Continued)

OTHER PUBLICATIONS

Chinese Office Action for 201210441765X dated Dec. 31, 2015.
(Continued)

*Primary Examiner* — Peter D Le
(74) *Attorney, Agent, or Firm* — Lerner, David, Littenberg, Krumholz & Mentlik, LLP (57) ABSTRACT

According to an illustrative embodiment an imaging system is provided. The system includes a lens tube; a first polarizing filter; and a second polarizing filter; wherein the first polarizing filter and the second polarizing filter are adjacent each other, and wherein a polarizing imparted by the first polarizing filter is different from a polarizing imparted by the second polarizing filter.

14 Claims, 10 Drawing Sheets

(51) Int. Cl.
    *G02B 5/20*     (2006.01)
    *G02B 27/28*     (2006.01)
    *G06T 3/40*     (2006.01)
    *H04N 5/225*     (2006.01)

(56) References Cited

U.S. PATENT DOCUMENTS

| | | |
|---|---|---|
| 5,447,513 A | 9/1995 | Davison et al. |
| 5,588,948 A | 12/1996 | Takahashi et al. |
| 5,649,897 A | 7/1997 | Nakamura et al. |
| 6,503,195 B1 | 1/2003 | Keller et al. |
| 8,078,048 B2 | 12/2011 | Kuroki |
| 2001/0012053 A1 | 8/2001 | Nakamura |
| 2002/0054431 A1 | 5/2002 | Costales |
| 2009/0278954 A1 | 11/2009 | Kanamori et al. |
| 2010/0238330 A1* | 9/2010 | Hirota ............... H01L 27/14621 348/273 |
| 2011/0033177 A1 | 2/2011 | Kuroki |
| 2012/0300037 A1 | 11/2012 | Laudo |

FOREIGN PATENT DOCUMENTS

| | | |
|---|---|---|
| JP | 07-020388 A | 1/1995 |
| JP | HEI08-304718 | 11/1996 |
| JP | 10-062697 A | 3/1998 |
| JP | H10248807 A | 9/1998 |
| JP | 2011035853 A | 2/2011 |
| JP | 2011139209 A | 7/2011 |
| JP | 2011145343 A | 7/2011 |
| WO | 96037796 A1 | 11/1996 |

OTHER PUBLICATIONS

Japanese Office Action for JP Application No. 2011248694, dated Aug. 11, 2015.

Japanese Office Action for JP Application No. 2011248694, dated Feb. 9, 2016.

* cited by examiner

FIG. 3B Baseline length of binocular disparity

IMAGING APPARATUS

CROSS-REFERENCE TO RELATED APPLICATION

The present application is a continuation of U.S. patent application Ser. No. 13/670,611, filed on Nov. 7, 2012, the disclosure of which claims priority from Japanese Patent Application No. JP 2011-248694 filed in the Japanese Patent Office on Nov. 14, 2011, the disclosure of which is incorporated herein by reference.

BACKGROUND

The present disclosure relates to an imaging apparatus that captures an image of a subject as a stereoscopic image.

In medical practice, for example, an image captured with use of an endoscope has been displayed on an eyepiece or a monitor receiver and observed to diagnose an affected part of a body. In addition, surgery under the use of an endoscope, which is performed while observing an image displayed on an eyepiece or a monitor receiver, has been rapidly diffused in recent years. In particular, the demand for an endoscope apparatus capable of stereoscopically showing an affected part of a body has increased.

For example, Japanese Patent Application Laid-open No. Hei 7-20388 (hereinafter, referred to as Patent Document 1) discloses an endoscope device configured to image a subject at a specified parallax angle by a stereoscopic imaging unit to obtain video signals, and independently display two images based on the video signals on both eyes of a user so that the user can stereoscopically view the subject.

In addition, Japanese Patent Application Laid-open No. Hei 10-62697 (hereinafter, referred to as Patent Document 2) discloses an endoscope device including a lens, a CCD (Charge Coupled Device), a drum, and a motor. The lens forms an image of an observed part via a diaphragm in an eyepiece. The CCD has an imaging surface at the image-forming position of the lens. The drum divides the image of the observed part, which is formed by the lens, into two of left and right parts and supplies them to the imaging surface of the CCD. The motor drives the drum to rotate.

SUMMARY

However, the endoscope device disclosed in Patent Document 1 uses two imaging optical systems including imaging lenses and CCD cameras, which leads to a problem of an increase in size of the device. Further, in the endoscope device disclosed in Patent Document 2, the drum and a rotation-drive system thereof are incorporated in its imaging optical system, and therefore the configuration becomes inevitably complicated.

In view of the circumstances as described above, it is desirable to provide an imaging apparatus with which a stereoscopic image of a subject is acquired and that has a simple configuration without increase in size.

An imaging system according to an illustrative embodiment includes a lens tube; a first polarizing filter; and a second polarizing filter; wherein the first polarizing filter and the second polarizing filter are adjacent each other, and wherein a polarizing imparted by the first polarizing filter is different from a polarizing imparted by the second polarizing filter.

As described above, according to the present disclosure, a stereoscopic image of a subject is acquired with an apparatus having a simple configuration without increase in size.

These and other objects, features and advantages of the present disclosure will become more apparent in light of the following detailed description of best mode embodiments thereof, as illustrated in the accompanying drawings.

DETAILED DESCRIPTION OF EMBODIMENTS

Hereinafter, embodiments of the present disclosure will be described with reference to the drawings.

First Embodiment (Imaging System)

Figure 1:
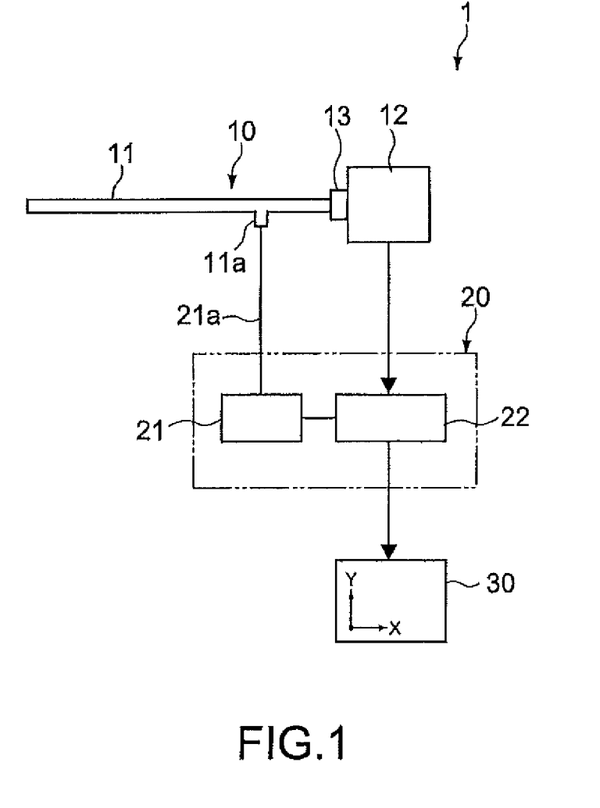
FIG. 1 is a schematic diagram showing a configuration of an imaging system including an imaging apparatus according to a first embodiment of the present disclosure.

FIG. 1 is a schematic diagram showing a configuration of an imaging system including an imaging apparatus according to a first embodiment of the present disclosure. In this embodiment, an example in which the imaging apparatus is applied to an endoscope apparatus used in medical practice will be described.

An imaging system 1 includes an endoscope apparatus 10, a control unit 20, and a monitor 30. Hereinafter, the imaging system 1 of this embodiment will be described.

The endoscope apparatus 10 includes a lens tube 11 and an imaging unit 12. The lens tube 11 is inserted into a body of a patient and irradiates an affected part of the body (subject) with illumination light. The imaging unit 12 receives reflected light, i.e., a light flux from the affected part of the subject (hereinafter, referred to as subject light flux), which is transmitted through the lens tube 11, converts the reflected light into an electrical signal to generate an image signal, and outputs the generated image signal to the control unit 20.

The control unit 20 includes a light source 21 and a signal processing unit 22. The light source 21 is connected to a light source connection unit 11a of the lens tube 11 via a light transmission member 21a such as an optical fiber and introduces illumination light to the lens tube 11. The signal processing unit 22 controls the light source 21 and processes the image signal output from the imaging unit 12. The signal processing unit 22 generates a stereoscopic image (three-dimensional image) of the affected part based on the image signal and outputs the image to the monitor 30. The monitor 30 includes a display unit (screen) having a horizontal direction in an X-axis direction and a vertical direction in a Y-axis direction orthogonal to the X-axis direction. The monitor 30 displays the stereoscopic image of the affected part on the display unit.

(Endoscope Apparatus)

Next, the endoscope apparatus 10 will be described in detail.

Figure 2:
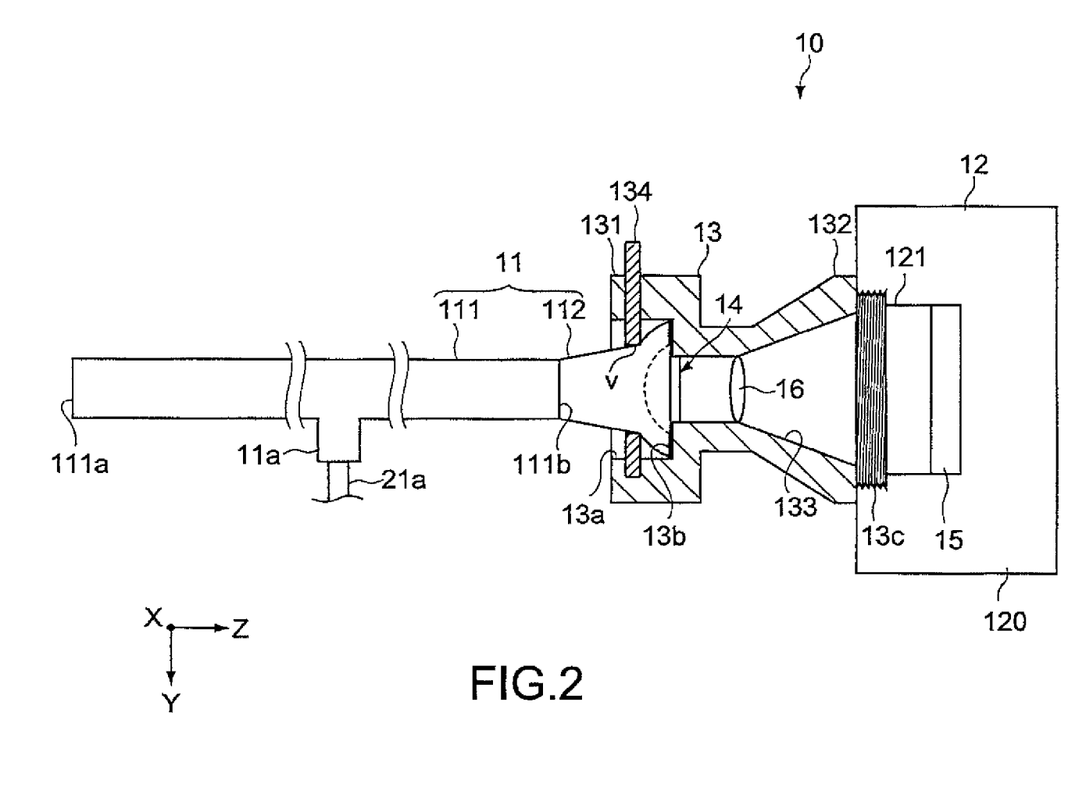
FIG. 2 is a schematic cross-sectional diagram showing the entire configuration of the imaging apparatus.

FIG. 2 is a schematic cross-sectional diagram showing the entire configuration of the endoscope apparatus 10. The endoscope apparatus 10 includes the lens tube 11, the imaging unit 12, and an adapter 13 (connection member).

The lens tube 11 includes a cylindrical rigid scope 111 having an axial center parallel to a Z-axis direction of FIG. 2, and an eyepiece 112.

Figure 3A:
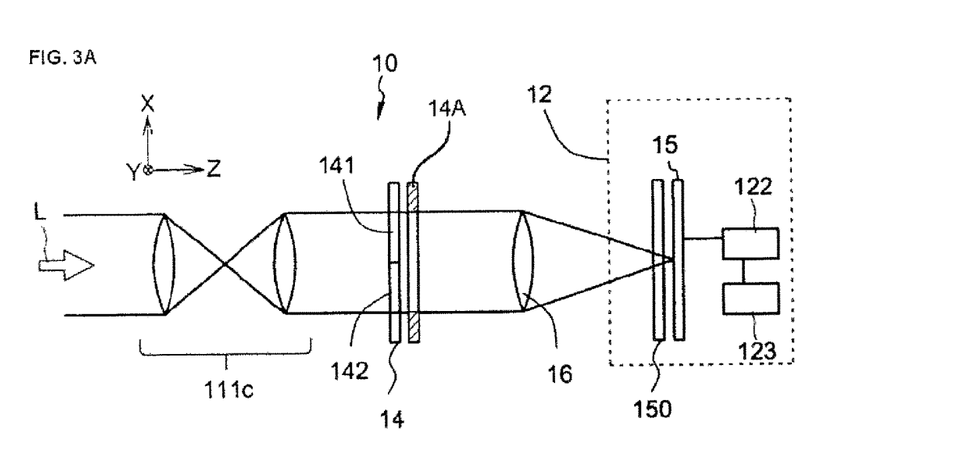
FIG. 3A is a schematic diagram showing an example of an optical system of the imaging apparatus.

The rigid scope 111 has a tip end 111a to be inserted into a body of a patient and a base 111b connected to the eyepiece 112. The tip end 111a is configured to emit illumination light and receive reflected light of the illumination light from the subject. The rigid scope 111 incorporates a light transmission path and an imaging optical system 111c (FIG. 3A). The illumination light introduced into the light source connection unit 11a is transmitted to the tip end 111a through the light transmission path. The imaging optical system 111c transmits a subject light flux that has been entered the tip end 111a to the base 111b.

The eyepiece 112 is used when the affected part of the body is observed under direct vision. The eyepiece 112 may include an eyepiece lens therein. In this embodiment, the imaging optical system 111c is configured such that an aperture position of the subject light flux corresponds to a position of a pupil of a user (doctor) who directly views the affected part via the eyepiece 112.

The imaging unit 12 includes a single-panel imaging device 15 having a light-receiving surface that receives the subject light flux. The imaging device 15 includes a plurality of pixels arrayed along the X-axis direction (horizontal direction) and the Y-axis direction (vertical direction), and is a solid-state imaging device such as a CCD (Charge Coupled Device) or a CMOS (Complementary Metal-Oxide Semiconductor). An array of wire grid polarizers is formed on the light-receiving surface of the imaging device 15, as described later.

The imaging unit 12 also includes a casing 120 that accommodates the imaging device 15, and the like. The casing 120 includes an opening 121 connected to the adapter 13. The imaging device 15 is arranged within the opening 121.

The adapter 13 includes a first connection end 131 connected to the eyepiece 112 of the lends tube 11, a second connection end 132 connected to the opening 121 of the imaging unit 12, and a hollow portion 133. The adapter 13 functions as a mounter for connecting the eyepiece 112 of the lens tube 11 to the imaging unit 12. For example, a C-mount adapter is used as the adapter 13.

The adapter 13 is detachably connected to the eyepiece 112. Accordingly, a common imaging unit may be used for various types of lens tubes that are different in length or diameter. In this embodiment, the adapter 13 includes a holder 134 that is attached to the first connection end 131 and is capable of engaging with the eyepiece 112 by an external operation. The second connection end 132 includes a screw portion 13c and is connected to the opening 121 of the imaging unit 12 via the screw portion 13c.

As shown in FIG. 2, the first connection end 131 of the adapter 13 includes a concave portion 13a that is capable of accommodating an end portion of the eyepiece 112. A reference surface 13b for positioning the eyepiece 112 is formed at the bottom of the concave portion 13a. The end portion of the eyepiece 112 abuts on the reference surface 13b, thus defining a relative position of the eyepiece 112 with respect to the adapter 13. The reference surface 13b is formed to be orthogonal to the Z axis. The holder 134 is for maintaining a state where the position of the eyepiece 112 with respect to the concave portion 13a is determined. The holder 134 is constituted of a plate-like member that is detachable from the first connection end 131 (concave portion 13a) in the Y-axis direction of FIG. 2 by an external operation, and includes an engagement portion v that is engaged with an outer circumference of the eyepiece 112 when the holder 134 is mounted to the concave portion 13a.

The hollow portion 133 is formed so as to penetrate the adapter 13 in the Z-axis direction and forms a path that guides the subject light flux emitted from the eyepiece 112 to the imaging device 15. A polarizing filter 14 and an imaging lens 16 are arranged in the hollow portion 133.

Figure 3B:
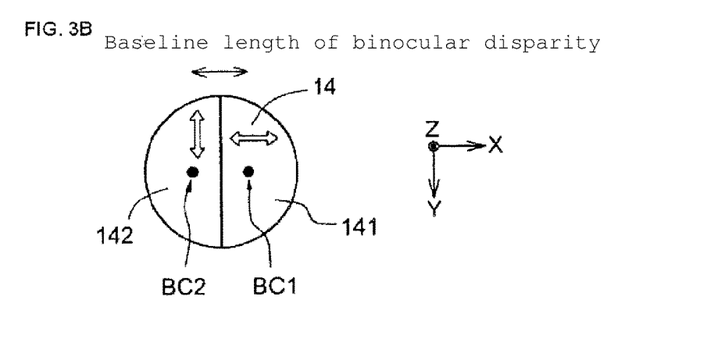
FIG. 3B is a schematic front diagram of a polarizing filter incorporated into the imaging apparatus.

The polarizing filter 14 includes two filter sections that separate the subject light flux projected from the eyepiece 112 into two polarization components. Specifically, the polarizing filter 14 includes a first filter section 141 and a second filter section 142 (FIG. 3B). The first filter section 141 allows a first polarization component of the subject light flux, which oscillates in the X-axis direction, to pass therethrough and blocks a second polarization component of the subject light flux, which oscillates in the Y-axis direction. The second filter section 142 blocks the first polarization component of the subject light flux and allows the second polarization component of the subject light flux to pass therethrough.

In this embodiment, the polarizing filter 14 is incorporated in the adapter 13 and disposed at the end portion of the eyepiece 112 so as to be aligned with the reference surface 13b of the first connection end 131. Accordingly, the polarizing filter 14 is automatically arranged in the vicinity of the eyepiece 112 when the adapter 13 is mounted to the eyepiece 112.

The imaging lens 16 is arranged between the polarizing filter 14 and the imaging device 15. The imaging lens 16 images the subject light flux that has passed through the polarizing filter 14 on the light-receiving surface of the imaging device 15.

FIG. 3A is a schematic diagram showing an example of an optical system of the endoscope apparatus 10.

The imaging optical system 111c includes a focus lens for focusing, a zoom lens for enlarging a subject, and the like, and is generally configured by combination of a plurality of lenses in order to correct chromatic aberration and the like. The polarizing filter 14 is arranged on an optical path of a subject light flux L. In this embodiment, the polarizing filter 14 is arranged at an aperture position 14A of the subject light flux L. At the aperture position, the subject light flux becomes parallel light of light coming from one point of the subject. Therefore, the polarizing filter 14 is arranged at the aperture position of the subject light flux, and the subject light flux of the parallel light is allowed to enter the polarizing filter 14. As a result, the subject light flux is properly separated for polarization.

FIG. 3B is a front diagram of the polarizing filter 14 when viewed from the Z-axis direction. The polarizing filter 14 includes the first filter section 141 and the second filter section 142 that are arranged along the X-axis direction. Specifically, the first filter section 141 and the second filter section 142 are arranged side by side in the horizontal direction of the display unit of the monitor 30. The first filter section 141 polarizes the subject light flux in the X-axis direction, and the second filter section 142 polarizes the subject light flux in the Y-axis direction. Therefore, a polarization state of first polarized light L1 that has passed through the first filter section 141 and that of second polarized light L2 that has passed through the second filter section 142 are different from each other.

Figure 3C:
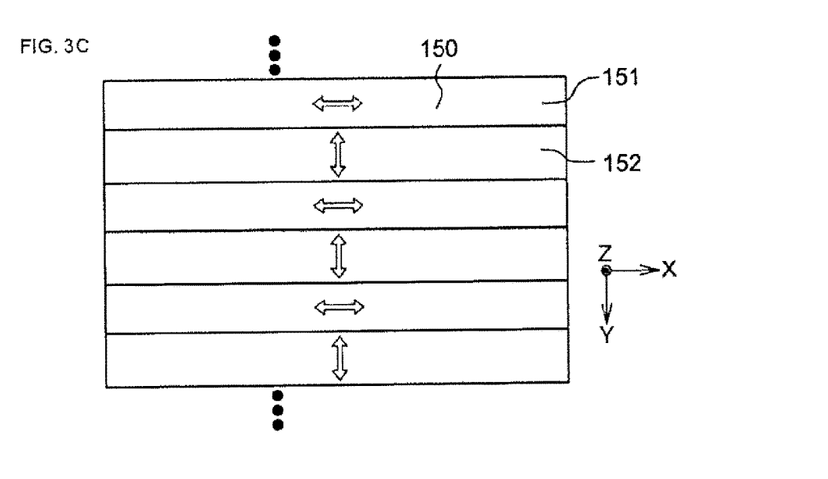
FIG. 3C is a schematic diagram showing a light-receiving surface of an imaging device incorporated in the imaging apparatus.

FIG. 3C is a schematic diagram showing a light-receiving surface 150 of the imaging device 15. The light-receiving surface 150 includes a plurality of first polarization areas 151 and second polarization areas 152 that are alternately arranged along the Y-axis direction (vertical direction) and extend in the X-axis direction (horizontal direction). The first polarization areas 151 each allow the first polarized light L1 of the subject light flux, which oscillates in the X-axis direction, to pass therethrough and block the second polarized light L2 of the subject light flux, which oscillates in the Y-axis direction. The second polarization areas 152 each block the first polarized light L1 of the subject light flux, which oscillates in the X-axis direction, and allow the second polarized light L2 of the subject light flux, which oscillates in the Y-axis direction, to pass therethrough. Therefore, the first polarized light L1 passes through the first polarization areas 151 to reach the imaging device 15, and the second polarized light L2 passes through the second polarization areas 152 to reach the imaging device 15.

The imaging device 15 captures an image so as to obtain a stereoscopic image in which a distance between a barycenter BC1 of the first filter section 141 and a barycenter BC2 of the second filter section 142 is set to be a baseline length of binocular disparity. The imaging unit 12 includes, in addition to the imaging device 15, for example, an image processing unit 122 and an image storage unit 123. The image processing unit 122 generates right-eye image data and left-eye image data based on electrical signals converted by the imaging device 15 and records the data in the image storage unit 123. It should be noted that the image processing unit 122 and the image storage unit 123 may be provided in the signal processing unit 22 of the control unit 20.

The outer shape of the polarizing filter 14 is circular. The first filter section 141 and the second filter section 142 each have an outer shape of a semicircle that occupies half the area of the polarizing filter 14. The boundary of the first filter section 141 and the second filter section 142 extends in the Y-axis direction. The polarizing filter 14 formed by combination of the two filter sections separates incident light into two different polarization states.

As described above, the polarizing filter 14 is constituted of polarizers that are bilaterally symmetrical and generates, at two positions bilaterally symmetrical in an upright state of the endoscope apparatus 10, polarization in linear directions orthogonal to each other or polarization in rotation directions opposite to each other. The first filter section 141 is a filter for polarizing the image of the subject that is assumed to be viewed by a right eye (light assumed to be received by the right eye). On the other hand, the second filter section 142 is a filter for polarizing the image of the subject that is assumed to be viewed by a left eye (light assumed to be received by the left eye).

In FIG. 3B, an orientation of an electric field of the first polarized light L1 (indicated by an outline arrow) is orthogonal to an orientation of an electric field of the second polarized light L2 (indicated by an outline arrow). Here, the orientation of the electric field of the first polarized light L1 is parallel to the X-axis direction. Specifically, for example, the first polarized light L1 mainly has a P wave (TM wave) as a polarization component, and the second polarized light L2 mainly has an S wave (TE wave) as a polarization component.

Additionally, as shown in FIG. 3C, the orientation of the electric field of the first polarized light L1 and the orientation of the electric field of the first polarization areas 151 (indicated by outline arrows) are parallel, and the orientation of the electric field of the second polarized light L2 and the orientation of the electric field of the second polarization areas 152 (indicated by outline arrows) are parallel. Further, an extinction ratio of the polarizers is favorably 3 or more, and more favorably, 10 or more.

In this embodiment, the outer shape of the polarizing filter 14 is a circle with a radius r of 10 mm. Further, the outer shape of the first filter section 141 and the second filter section 142 is a semicircle that occupies half the area of the polarizing filter 14. Therefore, the distance between the barycenter BC1 of the first filter section 141 and the barycenter BC2 of the second filter section 142 is [(8r)/(3π)] =8.5 mm.

Figure 4A:
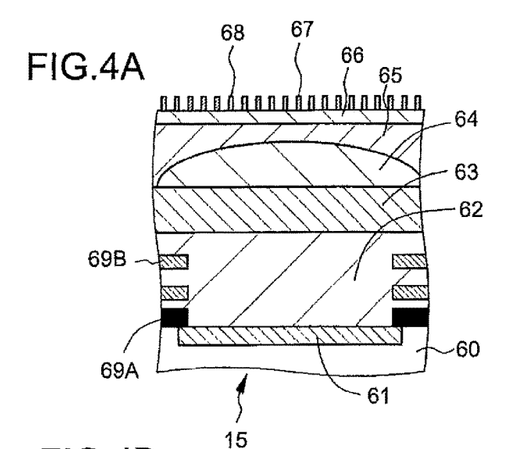
FIG. 4A is a cross-sectional diagram schematically showing a configuration of the imaging device.
Figure 4B:
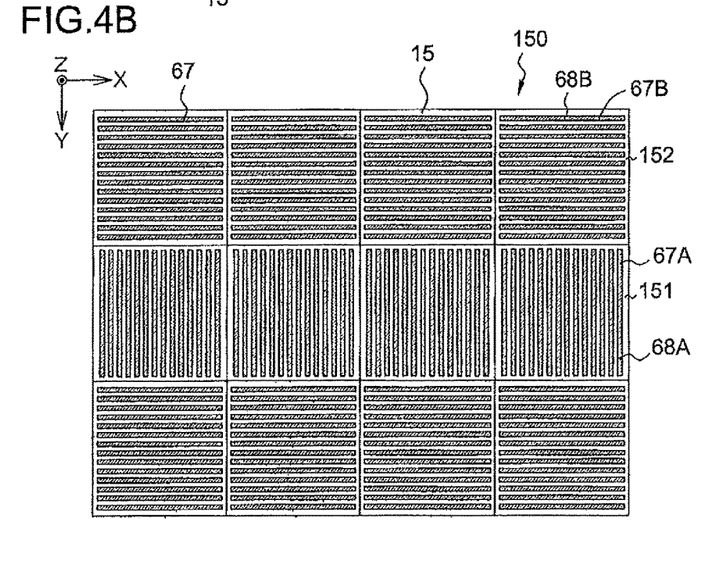
FIG. 4B is a schematic diagram showing the light-receiving surface of the imaging device.

The first polarization areas 151 and the second polarization areas 152 that are arranged on the light-receiving surface 150 of the imaging device 15 are each constituted of a wire grid polarizer. FIG. 4A is a cross-sectional diagram schematically showing a configuration of the imaging device 15, and FIG. 4B is a front diagram schematically showing an arrayed state of the first and second polarization areas 151 and 152 when viewed from the Z-axis direction.

The imaging device 15 has a structure in which, for example, a photoelectric conversion element 61 provided on a silicon semiconductor substrate 60, and thereon, a first planarization film 62, a color filter 63, an on-chip lens 64, a second planarization film 65, an inorganic insulation underlying layer 66, and wire grid polarizers 67 are laminated. The wire grid polarizers 67 form the first polarization areas 151 and the second polarization areas 152. In FIG. 4B, boundaries between pixels are indicated by solid lines.

A plurality of wires 68 that constitute the wire grid polarizers 67 extend in a direction parallel to the X-axis direction or the Y-axis direction. Specifically, in wire grid polarizers 67A that constitute the first polarization area 151, wires 68A extend in a direction parallel to the Y-axis direction. In wire grid polarizers 67B that constitute the second polarization area 152, wires 68B extend in a direction parallel to the X-axis direction. The direction orthogonal to the direction in which the wires 68 extend is used as a light transmission axis in the wire grid polarizers 67.

In this embodiment, an electrical signal used for obtaining right-eye image data is generated in the imaging device 15 by the first polarized light L1 that has passed through the first polarization areas 151 and reached the imaging device 15. Further, an electrical signal used for obtaining left-eye image data is generated in the imaging device 15 by the second polarized light L2 that has passed through the second polarization areas 152 and reached the imaging device 15. The imaging device 15 outputs those electrical signals at the same time or alternately in chronological order. The image processing unit 122 performs image processing on the output electrical signals (electrical signals for obtaining right-eye image data and left-eye image data, which have been output from the imaging device 15), and the resultant data are recorded in the image storage unit 123 as right-eye image data and left-eye image data.

Figure 5A:
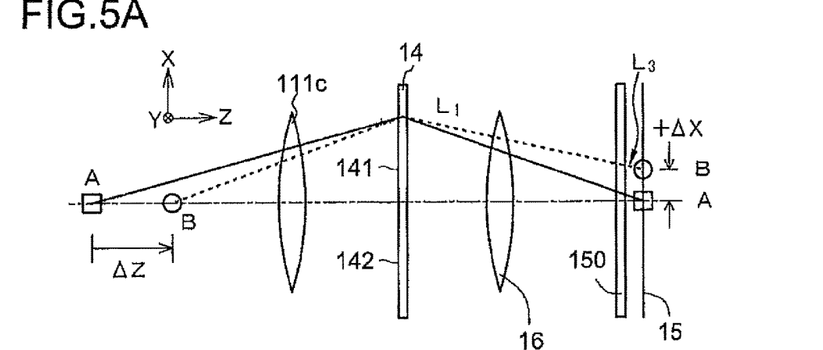
FIG. 5A and FIG. 5B are conceptual diagrams of light that reaches the imaging device from a subject.
Figure 5B:
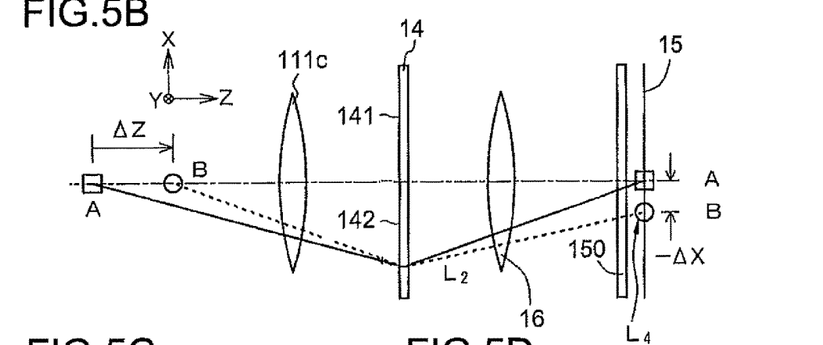
Figure 5C:
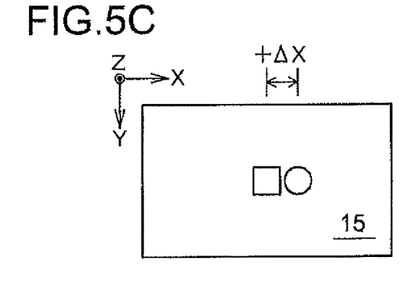
FIG. 5C and FIG. 5D are diagrams schematically showing images formed on the imaging device by the light shown in FIG. 5A and FIG. 5B.
Figure 5D:
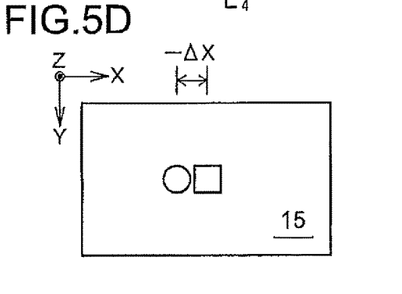

FIGS. 5A and 5B are conceptual diagrams of light that reaches the imaging device 15 from the subject, and FIGS. 5C and 5D are schematic diagrams showing images formed on the imaging device by the light shown in FIGS. 5A and 5B.

As schematically shown in FIGS. 5A and 5B, it is assumed that the imaging optical system 111c obtains focus on a rectangular object A, and a circular object B is located at a position closer to the imaging optical system 111c than the object A. An image of the rectangular object A is formed in focus on the imaging device 15. Further, an image of the circular object B is formed out of focus on the imaging device 15. In the example shown in FIG. 5A, on the imaging device 15, the image of the object B is formed at a position separate by a distance (+ΔX) from the right-hand side of the object A. On the other hand, as shown in the example of FIG. 5B, on the imaging device 15, the image of the object B is formed at a position separate by a distance (−ΔX) from the left-hand side of the object A. Therefore, a distance (2×ΔX) is used as information related to a depth of the object B. In other words, an amount and a direction of blurring of the object B, which is located closer to the endoscope apparatus than the object A, are different from those of an object located farther from the endoscope apparatus, and the amount of blurring of the object B differs depending on the distance between the object A and the object B.

Then, a stereoscopic image is obtained, in which the distance between the barycentric positions of the shapes of the first filter section 141 and the second filter section 142 of the polarizing filter 14 is set to be a baseline length of binocular disparity. In other words, the stereoscopic image is obtained by a well-known method, based on a right-eye image (see schematic diagram of FIG. 5C) and a left-eye image (see schematic diagram of FIG. 5D) that are obtained as described above. It should be noted that when right-eye image data is combined with left-eye image data, a normal two-dimensional (plane) image, which is not a stereoscopic image, is obtained.

Figure 6:
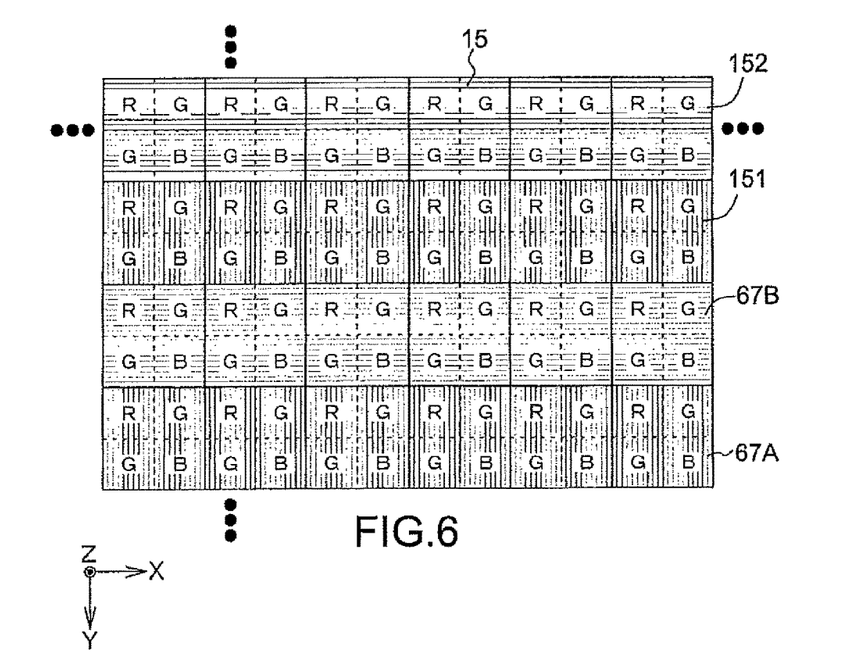
FIG. 6 is a conceptual diagram for explaining the light-receiving surface of the imaging device.

FIG. 6 is a conceptual diagram for explaining the light-receiving surface of the imaging device 15.

The imaging device 15 has a bayer array, in which one pixel is constituted of four sub-pixels (one red pixel R to receive red light, one blue pixel B to receive blue light, and two green pixels G to receive green light). The first polarization area 151 is arranged for a pixel group in one row arranged along the X-axis direction. Similarly, the second polarization area 152 is arranged for a pixel group in one row that is arranged along the X-axis direction and is adjacent to the former pixel group in the Y-axis direction. The first polarization areas 151 and the second polarization areas 152 are alternately arranged in the Y-axis direction.

The first polarization areas 151 and the second polarization areas 152 extend in the X-axis direction as a whole. A unit length of the first polarization areas 151 and second polarization areas 152 along the X-axis direction and Y-axis direction is equal to a length of the imaging device 15 along the X-axis direction and the Y-axis direction. With such a configuration, a band-like image extending in the X-axis direction based on the light mainly having a P-wave component (right-eye image) and a band-like image extending in the X-axis direction based on the light mainly having an S-wave component (left-eye image) are alternately generated along the Y-axis direction. In FIG. 6, vertical lines drawn in the first polarization areas 151 and transverse lines drawn in the second polarization areas 152 schematically show the wires of the wire grid polarizers 67A and 67B.

The electrical signals for each of the right-eye image data and the left-eye image data are generated along the Y-axis direction in every other row, as described above. In this regard, to generate the right-eye image data and the left-eye image data, the image processing unit 122 performs mosaic processing, e.g., super-resolution processing on the electrical signals, to eventually generate the right-eye image data and the left-eye image data. Further, the emphasis, optimization, and the like of disparity are also achieved by, for example, a disparity detection technique of generating a disparity map by stereo matching based on the left-eye image data and the right-eye image data, and a disparity control technique of controlling disparity based on a disparity map.

Figure 7:
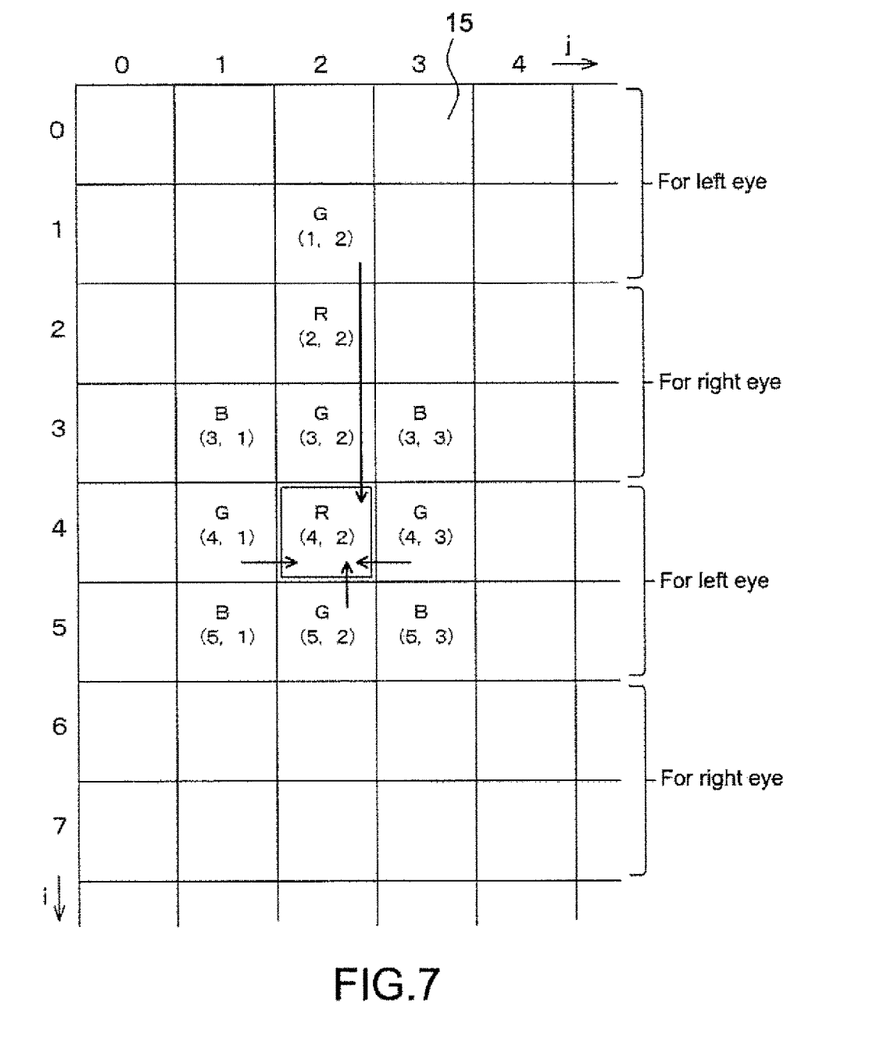
FIG. 7 is a conceptual diagram for explaining the light-receiving surface of the imaging device.

FIG. 7 is a conceptual diagram of the light-receiving surface with the bayer array, for explaining image processing (mosaic processing) of performing mosaic processing on electrical signals obtained from the imaging device to obtain signal values. FIG. 7 shows an example in which a signal value on a green pixel in the left-eye image is generated.

In normal demosaic processing, it is general to use a mean value of electrical signals of adjacent pixels of a single color. However, as in this embodiment, in the case where a pixel group (pixel row) for obtaining the right-eye image data and a pixel group (pixel row) for obtaining the left-eye image data are alternately repeated, there is a fear that original image data is not obtained when the values of adjacent pixels are used as they are. In this regard, demosaic processing is performed in consideration of whether an electrical signal of a pixel to be referred to corresponds to the right-eye image data or the left-eye image data.

It is assumed that in the bayer array, a red pixel R is arranged at a position (4,2). In this case, to generate a green-pixel signal value g' corresponding to the position (4,2), a calculation represented by the following expression is performed.

$$g'4,2=(g4,1+g4,3+g5,2+g1,2\times W3)/(3.0+W3)$$

In the expression, $g'i,j$ on the left side is a green-pixel signal value at a position $(i,j)$. Further, $gi,j$ on the right side is an electrical signal value of a green pixel at the position $(i,j)$. Furthermore, "3.0" corresponds to the sum of weights. Specifically, the weights are obtained when a distance (W1) from the pixel of interest R4,2 to each of adjacent pixels G4,1, G4,3, and G5,2 is set to, for example, "1.0" and reciprocals thereof are set as the weights. W3 is a weight for an electrical signal value of a pixel G1,2 that is distant by three pixels and is "⅓" in this case. When the above expression is generalized, the following expressions are obtained.

In the case where i is an even number (signal value of green pixel G corresponding to position of red pixel R, $$g'i,j=(gi,j-1\times W1+gi,j+1\times W1+gi+1,j\times W1+gi-3,j\times W3)/(W1\times 3.0+W3).$$

In the case where i is an odd number (signal value of green pixel G corresponding to position of blue pixel B), $$g'i,j=(gi,j-1\times W1+gi,j+1\times W1+gi+1,j\times W1+gi-3,j\times W3)/(W1\times 3.0+W3).$$

where W1=1.0 and W3=⅓.

The mosaic processing may also be performed on the red pixel R and the blue pixel B by the similar manner.

Pixel signal values at respective pixel positions are obtained by the demosaic processing, but in this stage, the signal values are arranged in every other row. Therefore, pixel signal values are to be generated for areas where pixel signal values are not provided, by interpolation (complement method). As interpolation techniques, a well-known method such as a method of using a mean value of values of adjacent pixels is used. This interpolation processing may be performed concurrently with the demosaic processing. The image quality is completely maintained in the X-axis direction, and accordingly the degradation in image quality, such as a reduction in resolution of the entire image, occurs relatively less frequently.

According to this embodiment, two different images divided in the horizontal direction by the polarizing filter 14 are simultaneously generated, and accordingly a stereoscopic image of an affected part of a body is acquired by one eye. Further, a compact endoscope apparatus 10 having a simple configuration and structure and a reduced number of components is provided. Furthermore, a plurality of sets of lenses and polarizing filters are unnecessary, and accordingly a displacement and a difference are not caused in zoom, aperture portion, focus, angle of convergence, and the like. In addition, since a baseline length of binocular disparity is relatively short, a natural stereoscopic effect is obtained. Additionally, when the polarizing filter 14 is configured to be detachable from the adapter 13, a two-dimensional image and a three-dimensional image are easily obtained.

Second Embodiment

Figure 8:
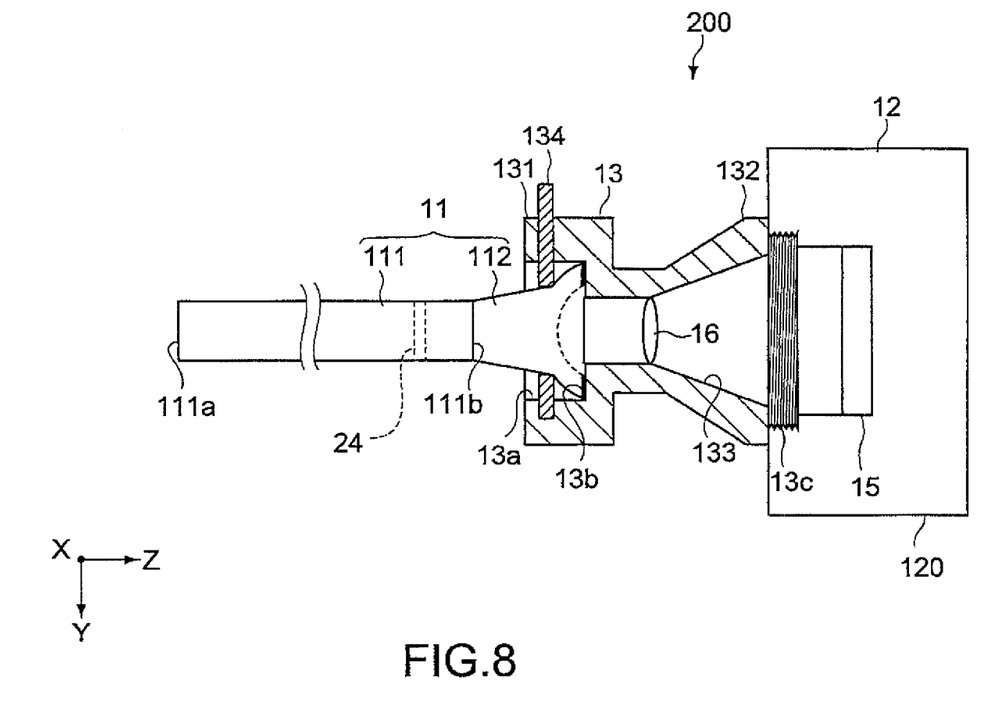
FIG. 8 is a schematic cross-sectional diagram showing the entire configuration of an imaging apparatus according to a second embodiment of the present disclosure.

FIG. 8 is a schematic cross-sectional diagram showing the entire configuration of an endoscope apparatus according to a second embodiment of the present disclosure. Hereinafter, a configuration different from that of the first embodiment will mainly be described, and the same components as those of the first embodiment will be denoted by the same reference symbols and the description thereof will be omitted or simplified.

An endoscope apparatus 200 of this embodiment is different from the endoscope apparatus 10 of the first embodiment described above in that a polarizing filter 24 is arranged within the rigid scope 111 of the lens tube 11. The polarizing filter 24 has the same configuration as that of the polarizing filter 14 described in the first embodiment and is arranged in an aperture portion (not shown) of a subject light flux in an imaging optical system within the rigid scope 111. The aperture portion has a function of increasing or decreasing an amount of light in order to adjust the amount of condensed light and is constituted by, for example, combination of a plurality of plate-like blades.

The polarizing filter 24 is arranged in the vicinity of the aperture portion. The polarizing filter 24 is arranged at a position as close as possible to the aperture portion as long as it does not interfere with the action of the aperture portion. With this configuration, the subject light flux of parallel light is allowed to enter the polarizing filter 24, with the result that the subject light flux is properly separated for polarization.

Also in the endoscope apparatus 200 configured as described above according to this embodiment, the same action and effect as those of the first embodiment described above are obtained.

Third Embodiment

Figure 9:
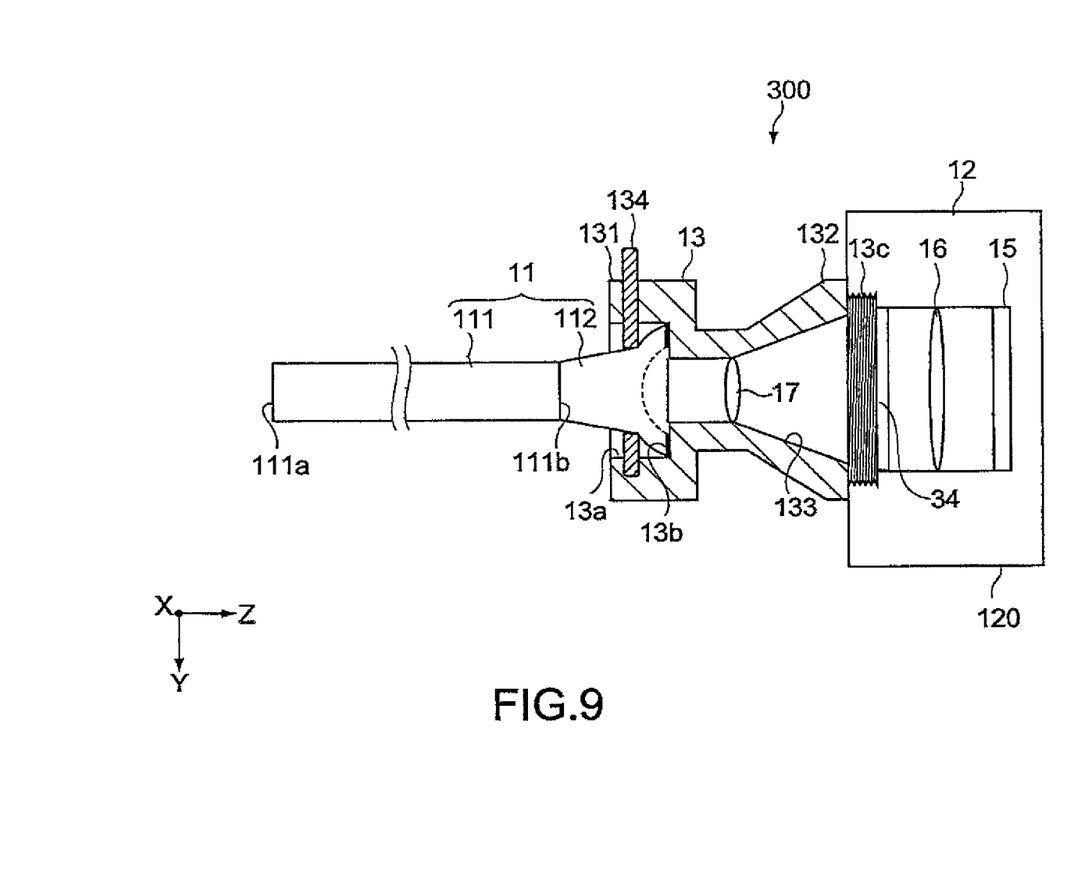
FIG. 9 is a schematic cross-sectional diagram showing the entire configuration of an imaging apparatus according to a third embodiment of the present disclosure.

FIG. 9 is a schematic cross-sectional diagram showing the entire configuration of an endoscope apparatus according to a third embodiment of the present disclosure. Hereinafter, a configuration different from that of the first embodiment will mainly be described, and the same components as those of the first embodiment will be denoted by the same reference symbols and the description thereof will be omitted or simplified.

An endoscope apparatus 300 of this embodiment is different from the endoscope apparatus 10 of the first embodiment described above in that a polarizing filter 34 is arranged within the casing 120 of the imaging unit 12. The polarizing filter 34 has the same configuration as that of the polarizing filter 14 described in the first embodiment and is arranged in an aperture portion (not shown) of a subject light flux in an imaging optical system within the casing 120. An optical component having the aperture function described above may be arranged at the aperture portion.

In this embodiment, the imaging lens 16 is arranged between the polarizing filter 34 and the imaging device 15. An optical lens 17 to project the subject light flux emitted from the eyepiece 112 to the polarizing filter 34 is arranged within the adapter 13.

Also in the endoscope apparatus 300 configured as described above according to this embodiment, the same action and effect as those of the first embodiment described above are obtained.

Hereinabove, the embodiments of the present disclosure have been described, but the present disclosure is not limited to the embodiments described above. The present disclosure can be variously modified as a matter of course without departing from the gist of the present disclosure.

For example, in the embodiments described above, each of the imaging apparatuses according to the embodiments of the present disclosure is applied to an endoscope apparatus used in medical practice has been described as an example. However, the present disclosure is not limited to the above example and is applicable to, for example, a microscope, an endoscope for industrial use, and the like.

Further, in the embodiments described above, the polarizing filter 14 is configured such that the orientation of the electric field of the first polarized light L1 is parallel to the X-axis direction, and the orientation of the electric field of the second polarized light L2 is parallel to the Y-axis direction. Instead, the polarizing filter may be configured such that the orientations of the respective electric fields of the first polarized light and the second polarized light form an angle of 45 degrees with respect to the X-axis direction and the Y-axis direction.

Figure 10A:
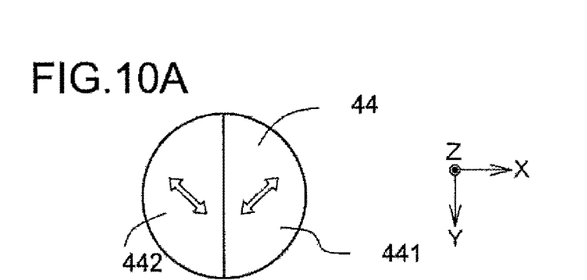
FIG. 10A is a diagram showing a modified example of the configuration shown in FIG. 3B.
Figure 10B:
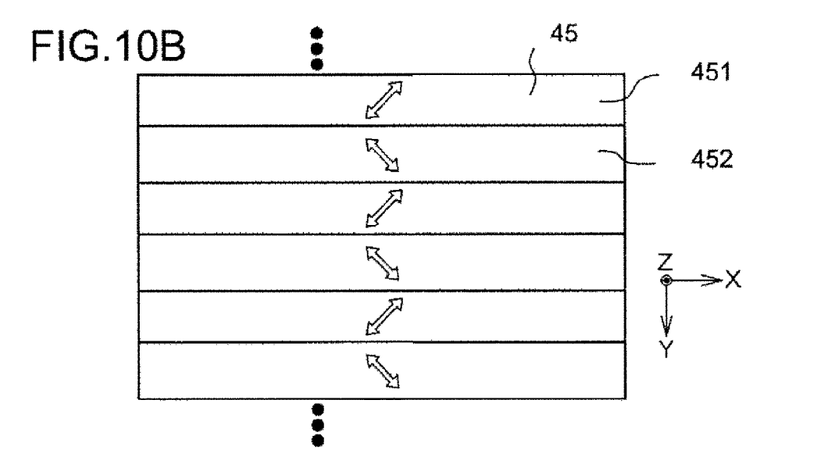
FIG. 10B is a diagram showing a modified example of the configuration shown in FIG. 3C.

FIG. 10A is a schematic diagram of a polarizing filter 44 configured as described above. A first filter section 441 and a second filter section 442 form first polarized light and second polarized light, respectively, each having an electric-field direction in a direction indicated by an outline arrow. Those first polarized light and second polarized light are composed of polarization components orthogonal to each other. In this case, a light-receiving surface of an imaging device 45 is provided with polarization areas as shown in FIG. 10B. A light transmission axis of first polarization areas 451 is parallel to the electric-field direction of the first polarized light, and a light transmission axis of second polarization areas 452 is parallel to the electric-field direction of the second polarized light. Those first polarization areas 451 and second polarization areas 452 are constituted of wire grid polarizers having the configuration as described above. Also in the configuration as described above, the same action and effect as those of the embodiments described above are obtained.

It should be noted that the present disclosure may be configured as follows.

(1) An imaging system including:
a lens tube;
a first polarizing filter; and
a second polarizing filter;
wherein the first polarizing filter and the second polarizing filter are adjacent each other, and wherein a polarizing imparted by the first polarizing filter is different from a polarizing imparted by the second polarizing filter.

(2) The imaging system according to (1), wherein the lens tube is removable.

(3) The imaging system according to (1), wherein the first polarizing filter and the second polarizing filter are removable.

(4) The imaging system according to (1), wherein the first polarizing filter and the second polarizing filter are arranged in close proximity to an aperture position of the imaging system.

(5) The imaging system according to (1), further including an imaging unit and an adapter connecting the imaging unit to the lens tube, and wherein the first polarizing filter and the second polarizing filter are positioned within the adapter.

(6) The imaging system according to (5), wherein the polarizing imparted by the first polarizing filter and the polarizing imparted by the second polarizing filter are linear.

(7) The imaging system according to (6), wherein the polarizing imparted by the first polarizing filter is orthogonal to the polarizing imparted by the second polarizing filter.

(8) The imaging system according to (5), wherein the polarizing imparted by the first polarizing filter and the polarizing imparted by the second polarizing filter are rotational.

(9) The imaging system according to (8), wherein the polarizing imparted by the first polarizing filter rotates in a direction opposite to the polarizing imparted by the second polarizing filter.

(10) The imaging system according to (5), further including an imaging device that is optically coupled to the lens tube.

(11) The imaging system according to (10), wherein the imaging device is a solid-state imaging device.

(12) The imaging system according to (10), wherein the imaging device includes a plurality of first polarization areas and a plurality of second polarization areas.

(13) The imaging system according to (12), wherein an orientation of the plurality of first polarization areas corresponds to one of the polarizing imparted by the first polarizing filter and the polarizing imparted by the second polarizing filter, and an orientation of the plurality of second polarization areas corresponds to another of the polarizing imparted by the first polarizing filter and the polarizing imparted by the second polarizing filter.

(14) The imaging system according to (12), wherein each of the first polarization areas and each of the second polarization areas includes a plurality of wire grid polarizers.

(15) The imaging system according to (5), further including an eyepiece lens positioned within the lens tube.

(16) The imaging system according to (15), further including an imaging device that is optically coupled to the eyepiece lens.

(17) The imaging system according to (5), wherein the imaging unit includes a solid-state imaging device and a casing.

(18) The imaging system according to (5), wherein the system is an endoscope.

(19) The imaging system according to (5), wherein the system is a microscope.

(20) The imaging system according to (1), wherein the first polarizing filter and the second polarizing filter are positioned within the lens tube.

(21) The imaging system according to (1), further including an imaging unit that is optically coupled to the lens tube, and wherein the first polarizing filter and the second polarizing filter are positioned within the imaging unit.

(22) The imaging system according to (21), wherein the imaging unit includes a solid-state imaging device and a casing.

(23) An imaging method including;
providing a lens tube; and
polarizing light within the lens tube using at least a first polarizing filter and a second polarizing filter, the first polarizing filter and the second polarizing filter being adjacent each other, and a polarizing imparted by the first polarizing filter being different from a polarizing imparted by the second polarizing filter.

(24) A non-transitory computer-readable medium having stored thereon a computer-readable program for implementing an imaging method, the method including:
providing a lens tube; and
polarizing light within the lens tube using at least a first polarizing filter and a second polarizing filter, the first polarizing filter and the second polarizing filter being adjacent each other, and a polarizing imparted by the first polarizing filter being different from a polarizing imparted by the second polarizing filter.

The present disclosure may also be configured as follows.

(1) An imaging apparatus, including:
a lens tube including an eyepiece and configured to transmit a subject light flux;
a polarizing filter arranged on an optical path of the subject light flux and including
a first filter section configured to allow a first polarization component of the subject light flux to pass therethrough, and block a second polarization component of the subject light flux, the first polarization component oscillating in a first direction, the second polarization component oscillating in a second direction orthogonal to the first direction, and
a second filter section configured to block the first polarization component of the subject light flux and allow the second polarization component of the subject light flux to pass therethrough; and
an imaging unit connected to the eyepiece and including an imaging device to receive the first polarization component and the second polarization component.

(2) The imaging apparatus according to (1), in which
the polarizing filter is arranged at an aperture position on the optical path.

(3) The imaging apparatus according to (1) or (2), in which
the polarizing filter is arranged in the eyepiece.

(4) The imaging apparatus according to any one of (1) to (3), further including
a connection member configured to connect the eyepiece and the imaging unit with each other, wherein
the polarizing filter is incorporated in the connection member.

(5) The imaging apparatus according to (4), in which
the connection member is detachable from the eyepiece.

(6) The imaging apparatus according to (4) or (5), in which
the polarizing filter is detachable from the connection member.

(7) The imaging apparatus according to any one of (1) to (6), in which
the imaging device includes a light-receiving surface on which a plurality of first polarizers and a plurality of second polarizers are arranged in matrix, the plurality of first polarizers being configured to allow the first polarization component to pass therethrough and block the second polarization component, the plurality of second polarizers being configured to block the first polarization component and allow the second polarization component to pass therethrough.

(8) The imaging apparatus according to (5), in which
the connection member includes a holder capable of engaging with the eyepiece by an external operation.

It should be understood by those skilled in the art that various modifications, combinations, sub-combinations and alterations may occur depending on design requirements and other factors insofar as they are within the scope of the appended claims or the equivalents thereof.

What is claimed is:

1. An endoscope apparatus to obtain an image of a part of a patient, said apparatus comprising:
   a lens tube;
   a removable polarizing structure arranged at a position of parallel light flux from the part of the patient transmitted through the lens tube; and
   an imaging portion configured to include
   (i) an imaging device to receive light passed through the removable polarizing structure, and
   (ii) circuitry configured to perform demosaic processing on an image signal generated by the imaging device,
   wherein the removable polarizing structure is detachable when the lens tube is connected to the imaging portion.

2. The endoscope apparatus of claim 1, wherein the removable polarizing structure includes a first polarizing structure having a first polarizing filter and a second polarizing filter, in which polarizing imparted by the first polarizing filter is different from polarizing imparted by the second polarizing filter.

3. The endoscope apparatus of claim 2, wherein the polarizing imparted by the first polarizing filter and the polarizing imparted by the second polarizing filter are linear.

4. The endoscope apparatus of claim 3, wherein the polarizing imparted by the first polarizing filter is orthogonal to the polarizing imparted by the second polarizing filter.

5. The endoscope apparatus of claim 2, wherein the polarizing imparted by the first polarizing filter and the polarizing imparted by the second polarizing filter are rotational.

6. The endoscope apparatus of claim 5, wherein the polarizing imparted by the first polarizing filter rotates in a direction opposite to the polarizing imparted by the second polarizing filter.

7. The endoscope apparatus of claim 2,
   wherein the image device includes a second polarizing structure having a plurality of first polarization areas and a plurality of second polarization areas.

8. The endoscope apparatus of claim 7, wherein an orientation of the plurality of first polarization areas corresponds to one of the polarizing imparted by the first polarizing filter and the polarizing imparted by the second polarizing filter, and an orientation of the plurality of second polarization areas corresponds to another of the polarizing imparted by the first polarizing filter and the polarizing imparted by the second polarizing filter.

9. The endoscope apparatus of claim 1, wherein the imaging device is a solid-state imaging device.

10. The endoscope apparatus of claim 1,
    wherein the image device includes a first polarizing structure having a plurality of first polarization areas and a plurality of second polarization areas, and
    wherein each of the first polarization areas and each of the second polarization areas comprises a plurality of wire grid polarizers.

11. The endoscope apparatus of claim 1, wherein the imaging device is optically coupled to the eyepiece lens.

12. The endoscope apparatus according to claim 1, wherein the imaging device has a bayer-array color filter.

13. The endoscope apparatus according to claim 1, further comprising:
    second circuitry configured to interpolate a target pixel based on adjacent pixels which are respectively located on a left-side, a right-side, an up-side, and a down-side of the target pixel.

14. The endoscope apparatus according to claim 1,
    wherein the image device includes a first polarizing structure having a plurality of first polarization areas and a plurality of second polarization areas,
    the apparatus further comprising:
    second circuitry configured to interpolate a target pixel based on only pixels that receive light passed through the first polarization areas.

* * * * *